US010314873B2

(12) United States Patent
Aharon et al.

(10) Patent No.: US 10,314,873 B2
(45) Date of Patent: Jun. 11, 2019

(54) METHOD OF TREATMENT OF DISEASES USING HOODIA EXTRACTS

(71) Applicants: HADASIT MEDICAL RESEARCH SERVICES & DEVELOPMENT LTD., Jerusalem (IL); DESERT LABS AGRICULTURE COOPERATIVE ASSOCIATION LTD., Kibbutz Yotvata (IL)

(72) Inventors: Refael Aharon, Modi'in (IL); Yaron Ilan, Jerusalem (IL)

(73) Assignees: HADASIT MEDICAL RESEARCH SERVICES & DEVELOPMENT LIMITED, Jerusalem (IL); DESERT LABS AGRICULTURE COOPERATIVE ASSOCIATION LTD., Eilot (IL)

(*) Notice: Subject to any disclaimer, the term of this patent is extended or adjusted under 35 U.S.C. 154(b) by 25 days.

(21) Appl. No.: 14/133,968

(22) Filed: Dec. 19, 2013

(65) Prior Publication Data

US 2014/0341952 A1 Nov. 20, 2014

Related U.S. Application Data

(63) Continuation of application No. 13/133,255, filed as application No. PCT/IL2009/001152 on Dec. 6, 2009, now abandoned.

(60) Provisional application No. 61/193,571, filed on Dec. 8, 2008.

(51) Int. Cl.
*A61K 36/24* (2006.01)
*A61K 36/27* (2006.01)
*A23G 9/42* (2006.01)
*A23L 33/105* (2016.01)

(52) U.S. Cl.
CPC .............. *A61K 36/27* (2013.01); *A23G 9/42* (2013.01); *A23L 33/105* (2016.08); *A23V 2002/00* (2013.01)

(58) Field of Classification Search
CPC .................................................. A61K 36/24
See application file for complete search history.

(56) References Cited

U.S. PATENT DOCUMENTS

| 7,033,616 | B2 | 4/2006 | Rubin et al. |
| 7,807,204 | B2* | 10/2010 | Alaoui Ismaili et al. .... 424/767 |
| 2005/0181077 | A1 | 8/2005 | Asiedu et al. |
| 2005/0276869 | A1* | 12/2005 | Bronner .................... 424/725 |
| 2006/0159773 | A1 | 7/2006 | Holt |
| 2006/0159779 | A1 | 7/2006 | Rubin et al. |
| 2007/0104805 | A1 | 5/2007 | Udell |

FOREIGN PATENT DOCUMENTS

| EP | 1 166 792 A2 | 1/2002 |
| JP | 2007330124 A | * 12/2007 |
| WO | 98/046243 A2 | 10/1998 |
| WO | WO 2006045112 A2 | * 4/2006 |

OTHER PUBLICATIONS

Revilla et al. (1998) J. Agric. Food Chem. 46, 4592-4597.*
Marchesini et al. (2003) Hepatology 37, 917-923.*
Marceau et al. (1999) J. Clin. Endocrinol. Metab. 84, 1513-1517.*
Landor et al. (2015) J. Med. Food 18(2): 250-258.*
Lynch et al. (2013) Food and Chemical Toxicology 56, 313-324.*
Van Heerden et al. (2007) Phytochemistry 68: 2545-2553.*
Zhao et al. (2011) Planta Med 77: 851-857.*
Landor et al. (2015) Journal of Medicinal Food 18(2): 250-258. (Year: 2015).*
Raskin et al. (2004) Current Pharmaceutical Design, 10, 3419-3429. (Year: 2004).*
Revilla et al. (1998) J. Agric. Food Chem. 46: 4592-4597. (Year: 1998).*
Tibe et al., "Potential for Domestication and Commercialization of Hoodia and Opuntia Species in Botswana," African Journal of Biotechnology, vol. 7, pp. 1199-1203, May 2, 2008.
Cortez-Pinto et al., "Non-Alcoholic Fatty Liver: Another Feature of the Metabolic Syndrome?," Clinical Nutrition, vol. 18, pp. 353-358, 1999.
Database WPI XP-002574669, Mar. 29, 2010.
Cortez-Pinto et al., "Alterations in Liver ATP Homeostasis in Human Nonalcoholic Steatohepatitis: A Pilot Study," JAMA, 1999, vol. 282, pp. 1659-1664.
Le et al., "Management of Non-Alcoholic Fatty Liver Disease and Steatohepatitis," Journal of Clinical and Experimental Hepatology, Jun. 2012, vol. 2, No. 2, pp. 156-173.
Rafiq et al., "Effects of Weight Loss on Nonalcoholic Fatty Liver Disease," Seminars in Liver Disease, vol. 28, pp. 427-433, 2008.
U.S. Department of Health and Human Services, Food and Drug Administration, Center for Food Safety and Applied Nutrition. "Dietary Supplements: New Dietary Ingredient Notifications and Related Issues: Guidance for Industry," Aug. 2016.
Ratziu, Vlad, et al. "Current Efforts and Trends in the Treatment of NASH," Journal of Hepatology, vol. 62, S65-S75, 2015.
Watkins, Paul B., et al. "Correspondence: Hepatic Dysfunction Associated with Troglitazone," The New England Journal of Medicine, vol. 338, No. 13, pp. 916-917, Mar. 26, 1998.

(Continued)

*Primary Examiner* — Christopher R Tate
*Assistant Examiner* — Russell G Fiebig
(74) *Attorney, Agent, or Firm* — Oliff PLC

(57) ABSTRACT

A method for treating a disease comprising administering to a mammal in need thereof an effective dosage of an extract of a plant of the genus *Hoodia*, wherein the disease is selected from the group consisting of immune-mediated disorders, immune-associated disorders, inflammatory diseases, coronary disease, insulin resistance and liver-related diseases. In a preferred embodiment, the *Hoodia* is *Hoodia parviflora*. Also disclosed is a pharmaceutical composition for treating the above diseases comprising an effective dosage of an extract of a plant of the genus *Hoodia*.

8 Claims, 5 Drawing Sheets

(56) References Cited

OTHER PUBLICATIONS

Caldwell, Stephen H., et al. "A Pilot Study of a Thiazolidinedione, Troglitazone, in Nonalcoholic Steatohepatitis," The American Journal of Gastroenterology, vol. 96, No. 2, Feb. 2001.

Comar, K.M., et al. "Review Article: Drug Therapy for Non-Alcoholic Fatty Liver Disease," Alimentary Pharmacology & Therapeutics, vol. 23, pp. 207-215, 2006.

Nair, S., et al. "Metformin in the Treatment of Non-Alcoholic Steatohepatitis: A Pilot Open Label Trial," Aliment Pharmacol Ther, vol. 20, pp. 23-28, 2004.

\* cited by examiner

METHOD OF TREATMENT OF DISEASES USING HOODIA EXTRACTS

CROSS-REFERENCE TO RELATED APPLICATIONS

This application is a continuation of U.S. patent application Ser. No. 13/133,255, filed Jun. 7, 2011, which is a National Phase Application of PCT International Application No. PCT/IL2009/001152, International Filing Date Dec. 6, 2009, claiming the benefit of U.S. Provisional Patent Application No. 61/193,571, filed Dec. 8, 2008, all of which are hereby incorporated by reference.

FIELD OF THE INVENTION

This invention relates to the use of plant parts and extracts of various species of the *Hoodia* plant for the treatment of various diseases. In particular, the invention relates to use of the species *Hoodia Parviflora*.

BACKGROUND OF THE INVENTION

*Hoodia*, from the Asclepiadaceae subfamily in the Apocynaceae family, is a succulent plant from Southern Africa that contains substances which suppress hunger, appetite, and thirst. The use of certain species of *Hoodia* as an appetite suppressant is supported by colorful folklore history and recent scientific studies. Tribesmen hunters in Africa have used *Hoodia* for many years to prevent hunger on long hunting trips.

WO 98/46243 discloses a process to extract a steroidal glycoside having a specified formula from plants of the Asclepiadaceae family, and in particular from the genus *Trichocaulon* or *Hoodia*, involving treating plant material with a solvent to extract a fraction having appetite suppressant activity, separating the extraction solution from the rest of the plant material, removing the solvent from the extraction solution and recovering the extract. The solvents specifically mentioned to perform the extraction are one or more of methylene chloride (dichloromethane), water, methanol, hexane, ethyl acetate or mixtures thereof.

U.S. Pat. No. 7,033,616 discloses pharmaceutical compositions containing an extract obtainable from a plant of the genus *Trichocaulon* or *Hoodia* having anti-diabetic activity. Also disclosed is a compound derived from the extract which may be used for the manufacture of medicaments having anti-diabetic activity.

U.S. Patent Application No. 2005/0181077 discloses a composition for treating AIDS. The composition comprises a medicament selected from an extract of at least one of a number of plant families including Asclepiadacea, which includes *Hoodia*, a glyceryl ester of any of the foregoing extracts; a saponin of any of the foregoing extracts; an alkaloid of any of the foregoing extracts; a protein of any of the foregoing extracts; a fat of any of the foregoing extracts; a sugar of any of the foregoing extracts; and any mixture of any of the foregoing.

U.S. Patent Application No. 2006/0159773 discloses herbal compositions containing *Hoodia gordonii* and synergistically enhancing ingredients such as green coffee bean extract. The compositions are useful in controlling obesity and supporting the treatment of various health conditions related thereto, including Syndrome X. This reference states that obesity is commonly associated with the metabolic Syndrome X, and that *Hoodia gordonii* has been proposed in the literature as a potentially valuable approach to the management of the metabolic Syndrome X. The main mechanism of action of *Hoodia gordonii* in the metabolic Syndrome X is appetite suppression, leading to control of calorie intake. This reference discloses that combinations of *Hoodia gordonii* and CGBE-containing chlorogenic acid or *Hoodia gordonii* and chlorogenic acid per se reduce insulin levels in Type II diabetes mellitus patients, patients with pre-diabetes, the metabolic Syndrome X and related conditions.

SUMMARY OF THE INVENTION

The present invention relates to a method for treating a disease comprising administering to a mammal in need thereof an effective dosage of an extract of a plant of the genus *Hoodia*, wherein the disease is selected from the group consisting of immune-mediated disorders, immune-associated disorders, inflammatory diseases, coronary heart disease, insulin resistance and liver-related diseases.

The term "*Hoodia*" as used herein may include any species of *Hoodia*, such as, but not limited to, *Hoodia parviflora*, *Hoodia gordonii*, *Hoodia macrantha*, *Hoodia currorii*, *Hoodia lugardii*, *Hoodia ruschii*, *Hoodia triebneri* and mixtures thereof, unless otherwise indicated. In a preferred embodiment, the Hoodia species is *Hoodia parviflora*.

An extract as used herein includes, but is not limited to, liquid extracts (frozen or liquid), solid extracts or spray-dried extracts, e.g. sap and plant solids. An extract as used herein may be purified, partially purified, concentrated and/or fractionated.

In one embodiment, the extract is an isolated compound having the biological properties of the extract, as defined below. In a preferred embodiment, the compound is not the compound named P57, an oxypregnane steroidal glycoside with the chemical name $(3\beta,12\beta,14\beta)$-3-[(O-6-Deoxy-3-O-methyl-$\beta$-D-glucopyranosyl-(1$\rightarrow$4)-O-2,6-dideoxy-3-O-methyl-$\beta$-D-ribo hexopyranosyl-(1$\rightarrow$4)-2,6-dideoxy-3-O-methyl-$\beta$-D-ribo-hexopyranosyl)oxy]-14-hydroxy-12-[[(2E)-2-methyl-1-oxo-2-butenyl]oxy]pregn-5-en-20-one. In another embodiment, P57 contributes to the biological properties of the extract, as defined below It has now been discovered that the extracts used in the invention possess a biological property which is capable of strengthening the immune system. This property of the extracts also has at times an anti-inflammatory effect. It has further been found that these biological properties are not due to the compound P57, verified by activity measurements.

In the present specification, the term biological properties or biological effect refers in general to the capability to treat a disease as defined below, in particular by strengthening the immune system, and to various biological effects, e.g. as demonstrated in the examples. In one embodiment, the above terms refer to strengthening the metabolic system.

The diseases included within the invention include immune-mediated and immune-associated disorders, inflammatory diseases, coronary disease, insulin resistance and liver-related diseases. In a preferred embodiment, the disease is not type II diabetes. In one alternative of this embodiment, the disease is diabetes when the *Hoodia* is *Hoodia parviflora*. In another preferred embodiment, the disease is not metabolic syndrome. In another preferred embodiment, the disease is not obesity or a disease treatable by appetite suppression.

The immune-mediated and/or immune-associated disorders may include autoimmune diseases, rheumatoid arthritis, acute and chronic graft versus host disease, systemic lupus erythmatosus, scleroderma, multiple sclerosis, hyperlipidemia, atherosclerosis, obesity, inflammatory bowel disease and immune mediated hepatitis, and any brain, lung, heart, gastrointestinal system, kidney, skin, muscle and nerve disorders that are mediated at least in part by the immune system, whether adaptive or innate. In addition any brain, lung, heart, gastrointestinal system, kidney, skin, muscle and nerves disorders that are mediated at least in part by the immune system, whether adaptive or innate are included.

Examples of coronary related-diseases are atherosclerosis and pathological triglyceride (TG) serum levels (hypertriglyceridemia).

The liver-related diseases may include hyperlipidemia, fatty-infiltration, non-alcoholic fatty liver disease (NAFLD), cirrhosis of the liver, hepatitis B, hepatitis C, autoimmune hepatitis, primary biliary cirrhosis (PBC), primary sclerosing cholangitis (PSC), end stage liver disease inflammation of and decrease in liver function, and in general any type of liver disease including immune mediated, viral, metabolic and drug induced. NAFLD includes non alcoholic steatohepatitis (NASH).

Examples of autoimmune diseases include multiple sclerosis (MS), autoimmune uveitis, autoimmune uveoretinitis, autoimmune thyroiditis, Hashimoto's disease, insulitis, Sjogren's syndrome, spontaneous abortions, experimental autoimmune myocarditis, rheumatoid arthritis (RA), inflammatory bowel disease (IBD), Crohn's disease, lupus (SLE), psoriasis and diabetes, particularly type I.

Additional examples of autoimmune diseases include Acute necrotizing hemorrhagic leukoencephalitis, Addison's disease, Agammaglobulinemia, Allergic asthma, Allergic rhinitis, Alopecia greata, Amyloidosis, Ankylosing spondylitis, Anti-GBM/Anti-TBM nephritis, Antiphospholipid syndrome (APS), Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune thrombocytopenic purpura (ATP), Axonal & neuronal neuropathies, Bal's disease, Behnet's disease, Bullous pemphigoid, Cardiomyopathy, Castleman disease, Celiac sprue (nontropical), Chagas' disease, Chronic fatigue syndrome, Chronic inflammatory demyelinating polyneuropathy (CIDP), Churg-Strauss syndrome, Cicatricial pemphigoid/benign mucosal pemphigoid, Cogan's syndrome, Cold agglutinin disease, Congenital heart block, Coxsackie myocarditis, CREST disease, Essential mixed cryoglobulinemia, Demyelinating neuropathies, Dermatomyositis, Devic disease, Discoid lupus, Dressler's syndrome, Endometriosis, Eosinophilic fasciitis, Erythema nodosum, Experimental allergic encephalomyelitis, Evan's syndrome, Fibromyalgia, Fibrosing alveolitis, Giant cell arteritis (temporal arteritis), Goodpasture's syndrome, Graves' disease, Guillain-Barr syndrome, Hemolytic anemia, Henoch-Schonlein purpura, Herpes gestationis, Hypogammaglobulinemia, Idiopathic thrombocytopenic purpura (ITP), IgA nephropathy, Immunoregulatory lipoproteins, Inclusion body myositis, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lyme disease, Meniere's disease, Microscopic polyangiitis, Mixed connective tissue disease (MCTD), Mooren's ulcer, Mucha-Habermann disease, Myasthenia gravis, Myositis, Narcolepsy, Neutropenia, Ocular cicatricial pemphigoid, Osteoarthritis, Palindromic rheumatism, Paraneoplastic cerebellar degeneration, Paroxysmal nocturnal hemoglobinuria (PNH), Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Psoriatic arthritis, Idiopathic pulmonary fibrosis, Pyoderma gangrenosum, Pure red cell aplasia, Raynaud's phenomenon, Reflex sympathetic dystrophy, Reiter's syndrome, Relapsing polychondritis, Restless legs syndrome, Rheumatic fever, Sarcoidosis, Schmidt syndrome, Scleritis, Scleroderma, Sperm & testicular autoimmunity, Stiff person syndrome, Subacute bacterial endocarditis (SBE), Sympathetic ophthalmia, Takayasu's arteritis, Temporal arteritis/Giant cell arteritis, Thrombocytopenic purpura (TTP), Autoimmune thyroid disease, Tolosa-Hunt syndrome, Transverse myelitis & necrotizing myelopathy, Ulcerative colitis, Undifferentiated connective tissue disease (UCTD), Vasculitis, Vesiculobullous dermatosis, Vitiligo and Wegener's granulomatosis.

Inflammatory diseases include sepsis, endotoxemia, pancreatitis, uveitis, hepatitis, peritonitis, keratitis, SIRS and injury-induced inflammation.

The method of the invention may involve any of the standard means of administration such as intravenous, intramuscular, intraperitoneal, topical, transdermal, buccal, sublingual, oral (po), subcutaneous, etc. In a preferred embodiment, the extracts are administered orally.

The present invention also relates to pharmaceutical compositions. A pharmaceutical composition as used herein means a composition comprising an extract of the invention, in admixture with acceptable auxiliaries such as, but not limited to, pharmaceutically acceptable carriers, diluents, adjuvants, excipients, or vehicles, such as preserving agents, fillers, disintegrating agents, wetting agents, emulsifying agents, suspending agents, sweetening agents, flavouring agents, perfuming agents, antibacterial agents, antifungal agents, lubricating agents and dispensing agents, depending on the nature of the mode of administration and dosage forms. The auxiliaries must be "acceptable" in the sense of being compatible with the other ingredients of the composition and not deleterious to the recipients thereof, i.e. pharmaceutically acceptable.

"Pharmaceutically acceptable" means it is, within the scope of sound medical judgement, suitable for use in contact with the cells of humans and animals without undue toxicity, irritation, allergic response and the like, and are commensurate with a reasonable benefit/risk ratio.

"Pharmaceutically acceptable dosage forms" as used herein include, but are not limited to dosage forms such as tablets, dragees, powders, elixirs, syrups, liquid preparations, including suspensions, sprays, lozenges, emulsions, solutions, granules and capsules, including liposome preparations. The active ingredient may also be presented as a bolus or paste. Techniques and formulations generally may be found in Remington, Pharmaceutical Sciences, Mack Publishing Co., Easton, Pa., latest edition.

Extracts of the invention and compositions comprising such extracts may be administered under the supervision of a medical specialist, or may be self-administered.

The exact dose and regimen of administration of an extract of the invention or a composition comprising such extract (an effective dosage or an amount effective in bringing about the biological effect) will necessarily be dependent upon the effect to be achieved (e.g. reduction in inflammation) and may vary with the route of administration, and the age and condition of the individual subject to whom the extract is to be administered.

A dosage for humans is likely to contain from about 10 to about 10,000 mg (dry weight) per 70 kg body weight per day. The desired dose may be presented as one dose or as multiple sub-doses administered at appropriate intervals.

The compositions may be prepared by any method well known in the art of pharmacy.

Such methods include the step of bringing in association a *Hoodia* extract of the invention with any auxiliary agent.

The invention further includes a pharmaceutical composition comprising an extract of the invention, in combination with packaging material, including instructions for the use of the composition for a use as hereinbefore described.

Extracts of the invention may be administered in conjunction with other ingredients, including, but not limited to folic acid, vitamins, minerals, anti-oxidants, other extracts from plants or fruit, liquid flavors and so forth.

Liquid flavors as used herein means any liquid flavor characterized by low viscosity.

Vitamins as used herein means any vitamin such as, but not limited to, B1, B2, B3, B6, B12, Folic Acid, Vitamin C, Biotin, Pantothenic acid, K, A, D, E and so forth.

Antioxidants as used herein are meant to encompass any antioxidant such as, but not limited to a compound that has antioxidant activity.

Minerals as used herein means any mineral such as, but not limited to, Na, K, Cl, Ca, P, Mg, Fe, I, Cu, Zn, Mn, Fl, and so forth.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Preparation of an Extract of *Hoodia parviflora*

The *Hoodia parviflora* extract used in the experiments described below was prepared as follows:

Fresh *Hoodia parviflora* plants were washed in water and disinfectant. The washed plants were frozen and cut to size of 0.1-10 cm², and 5-120% (v/v) water was added to the cut *Hoodia* plant tissue thereby obtaining suspended *Hoodia parviflora*. The suspended *Hoodia parviflora* plant tissue was further disintegrated and homogenized for 30 minutes in an ultrasonic bath filled with water at 0-10° C. Liquid *Hoodia* filtrate was separated from solid *Hoodia* sediment by centrifuging or filtering, thereby obtaining a 'liquid *Hoodia* extract' and a 'solid *Hoodia* extract'. All steps were carried out below 20° C.

Example I

Autoimmune Hepatitis

The administration of the plant lectin, concanavalin A (ConA) to mice induces a severe immune-mediated hepatitis within 20 hours. When injected intravenously to mice, ConA induces activation of T cells in the liver, NKT (natural killer T) cells being the most important. Together with Kupffer cells, NKT cells secrete large amounts of various hepatotoxic cytokines (IFN-γ and TNF-α) which cause severe hepatic inflammation.

Induction of ConA Hepatitis. The ConA (MP Biomedicals, USA) was dissolved in 50 mM Tris (pH 7), 150 mM NaCl, and 4 mM CaCl₂, and was intravenously injected into C57Bl/6 male mice, 10-12 weeks of age (500 µg per mouse) in a total volume of 250 µl. ConA was injected 20 h before sacrificing the mice.

Figure 1:
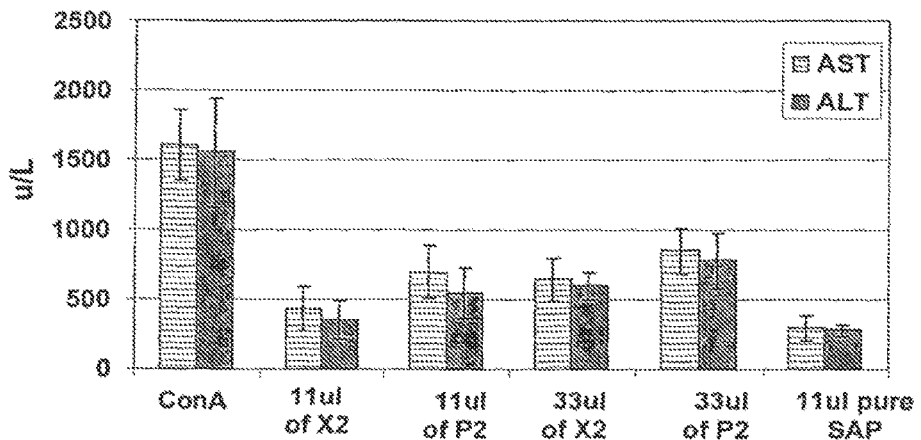
FIGS. 1 & 2 are bar graphs showing serum levels (u/L) of the liver enzymes aspartyl transaminase (AST) and alanine aminotransferase (ALT) in mice fed the amounts and types of *Hoodia* indicated.
Figure 2:
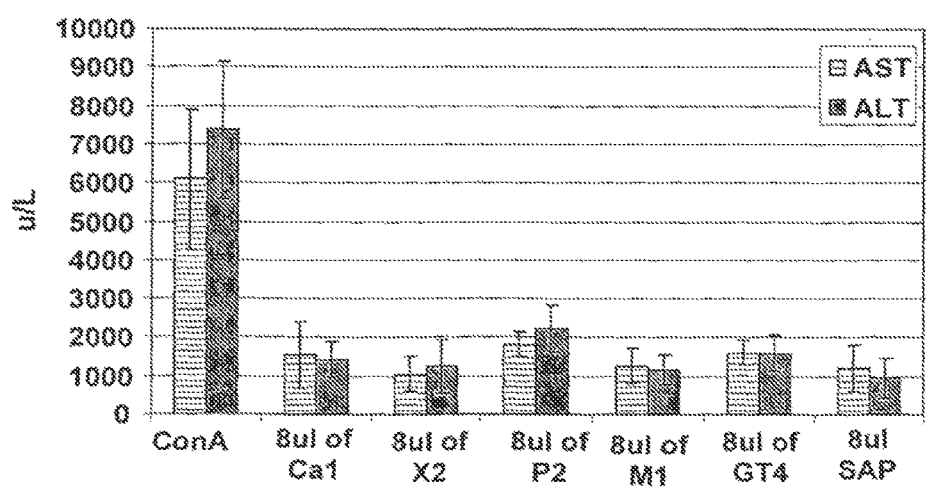

The administration of the *Hoodia* liquid extracts was oral (po). The exact volumes are described in FIGS. 1, 2 and 3. 5 mice per group were used. The following groups were tested in this and in the following examples (as indicated):
ConA, DDW—control (no *Hoodia*);
X2—pure *Hoodia Gordonii* from Africa
P2—*Hoodia Parviflora* from Africa
SAP—sap from *Hoodia Parviflora* (P2)
M1—*Hoodia Macrantha*
GT2,GT4—hybrid *Hoodia Gordonii*

The mice were sacrificed and their liver enzymes were measured. Evaluation of serum aspartyl transaminase (AST) and alanine aminotransferase (ALT) activities were determined using an automatic analyzer. Serum IFN-γ was measured using an ELISA assay (R&D, USA). The results are summarized in FIGS. 1, 2 and 3.

Figure 3:
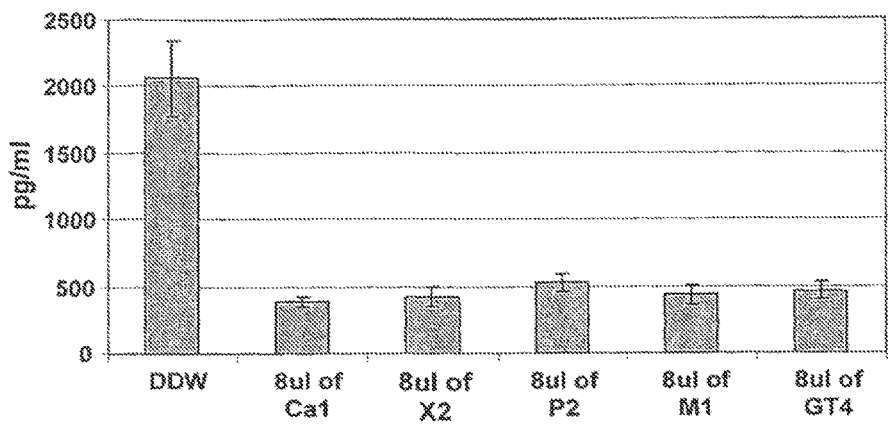
FIG. 3 is a bar graph showing IFN-γ levels (pg/ml) in mice as described in FIGS. 1 and 2.

It can be seen that the groups fed with *Hoodia* exhibited normal or near-normal serum levels of liver enzymes and IFN-γ. Thus, the *Hoodia* extracts reduced liver damage in mice suffering from autoimmune hepatitis as noted by a significant decrease in ALT levels in mice. It also appears that the mice fed smaller amounts of *Hoodia* extract exhibited a greater reduction in liver damage. FIG. 3 shows that the anti inflammatory effect of the different extracts tested was mediated by a decrease in IFN-γ levels.

Example II

P57 Content of Different *Hoodia* Extracts

The level of the compound P57 was measured in various *Hoodia* liquid extracts. The results are provided in the table below.

| *Hoodia* species | P57 (ug/ml) |
|---|---|
| *Hoodia Parviflora* from Africa (P1) | 175, 355 |
| *Hoodia Gordonii* from Africa (X3) | 2600, 2820 |

It can be seen that the level of P57 in *Hoodia Gordonii* is approximately 10× higher than in *Hoodia Parviflora*. Despite this significant difference, the effect on autoimmune hepatitis (and on other diseases as described below) was similar with the two plant varieties. This proves that the biological properties of the extract are not due to P57.

Example III

Fatty Liver Disease

Non-alcoholic fatty liver disease (NAFLD) is fatty inflammation of the liver when this is not due to excessive alcohol use. Non-alcoholic steatohepatitis (NASH) is the most extreme form of NAFLD, which is regarded as a major cause of cirrhosis of the liver of unknown cause.

Work with genetically obese, insulin-resistant ob/ob mice demonstrates that hepatocytes become steatotic and die at increased rates. Thus, ob/ob mice develop NASH spontaneously. Insulin resistance, the inability of insulin to appropriately stimulate glucose uptake, is a hallmark of type 2 diabetes mellitus. Hepatic steatosis results from lipid accumulation within hepatocytes due to variable combinations of excess lipid uptake and synthesis and altered lipid secretion.

The effect of *Hoodia* extracts on liver damage was assessed by the glucose tolerance test (GTT) and by determining hepatic triglyceride content.

Leptin deficient ob/ob mice (6-8 mice per group) received daily po administrations (11 ml doses) of water, P2, SAP or GT2 for 4 weeks.

| N = 6 | N = 8 | N = 8 | N = 8 |
|---|---|---|---|
| Control (water) | P2 | SAP | GT2 |

Figure 4:
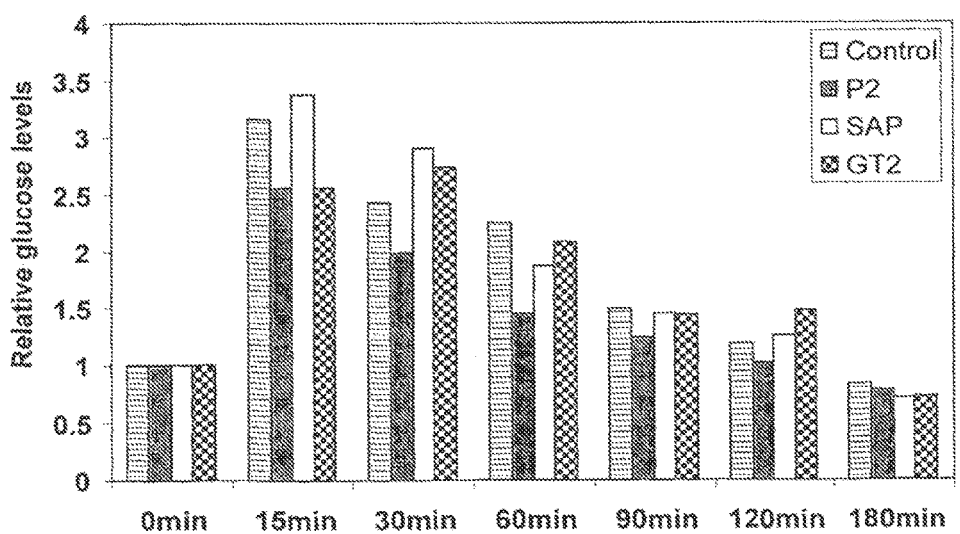
FIG. 4 is a bar graph showing relative glucose levels in different groups of ob/ob mice at various time points after glucose administration.

The mice were deprived of food for 12 hours and then given glucose. The serum glucose level was measured using Bayer Health Care strips at pre-determined times after administration of the glucose, as indicated in FIG. 4. The results for each group were normalized to 1, being the level of glucose at 0 minutes after administration. The results are summarized in FIG. 4.

It can be seen that the *Hoodia Parviflora* extract improved glucose tolerance in these mice.

Figure 5:
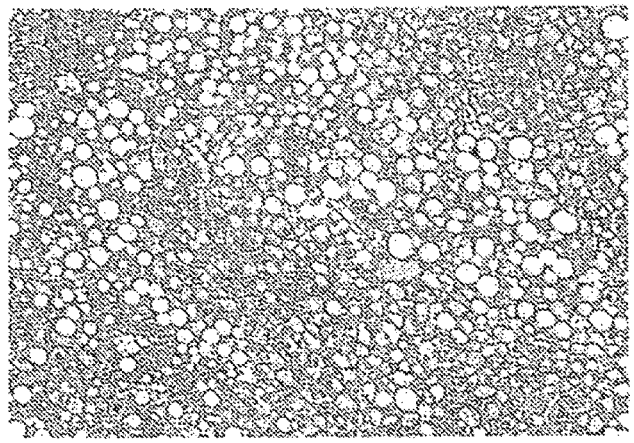
FIGS. 5 & 6 are stained liver tissue sections taken from control and *Hoodia* fed mice, respectively.
Figure 6:
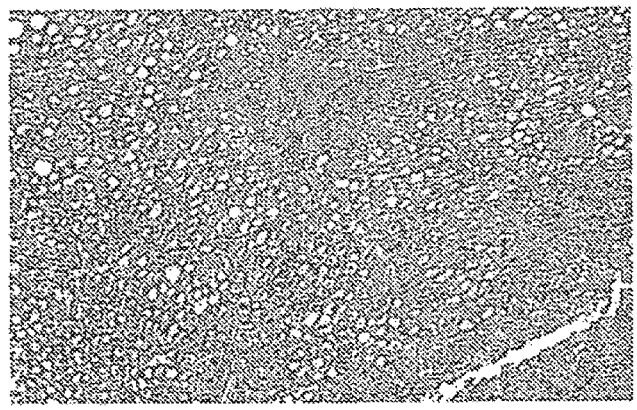

The liver morphology of these mice is shown in FIGS. 5 and 6. The liver tissue sections were stained with Hematoxylin-Eosin (H&E) stain. FIG. 5 is from a control mouse while FIG. 6 is from a P2 mouse. It can be seen that administration of *Hoodia Parviflora* significantly decreased hepatic fat content.

Figure 7:
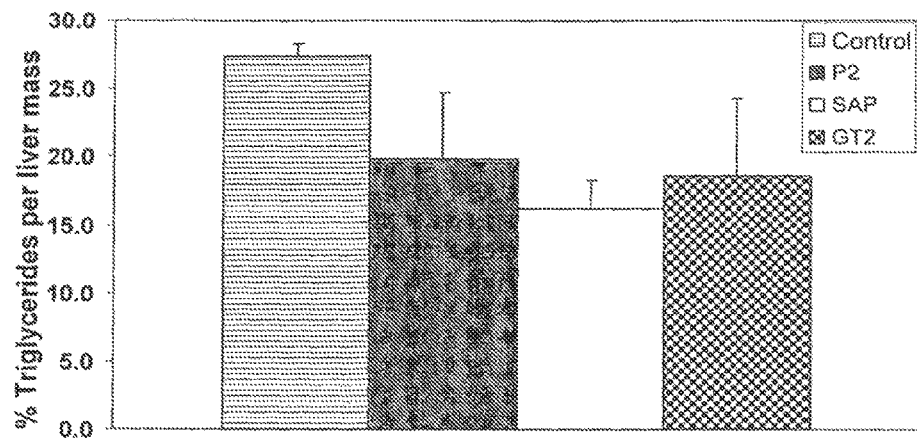
FIG. 7 is a bar graph showing % triglycerides per liver mass in different groups of ob/ob mice.

In order to further determine hepatic fat levels, liver triglycerides (TG) were measured. The mice were sacrificed and a liver lysate was prepared. TG in the lysate (Sigma) were measured. The results are shown in FIG. 7.

It can be seen that all *Hoodia* extracts significantly reduced hepatic TG content.

In summary, it may be seen that oral administration of *Hoodia* extracts to OB/OB mice: (1) decreases glucose levels; (2) decreases liver enzymes; (3) decreases triglyceride content in the liver; (4) decreases fat accumulation in the liver.

Example IV

ATP Measurements

P57 was isolated from *Hoodia gordonii* and found to have homologies to the steroidal core of cardiac glycosides. Intracerebroventricular (icv) injections of the purified P57 demonstrated that the compound has a likely central nervous system (CNS) mechanism of action. The studies demonstrated that the compound increases the content of ATP by 50-150% in hypothalamic neurons. Liver ATP content was also significantly reduced by about 60%.

A possible mechanism for the hypothalamic Na/K-ATPase activity is that hypothalamic regulation of food intake alters intracellular concentrations of ATP. While ATP may have direct effects on K+ channel activity or Na/K-ATPase, many other phosphorylation-dependent transduction pathways may mediate the subsequent integrative response to energy sensing.

The mechanisms that drive progression from fatty liver to steatohepatitis and cirrhosis are unknown. In animal models, obese mice with fatty livers are vulnerable to liver adenosine triphosphate (ATP) depletion and necrosis, suggesting that altered hepatic energy homeostasis may be involved. It has been shown that recovery from hepatic ATP depletion becomes progressively less efficient as body mass increases in healthy controls and is severely impaired in patients with obesity-related nonalcoholic steatohepatitis (Helena Cortez-Pinto, et al. *Alterations in Liver ATP Homeostasis in Human Nonalcoholic Steatohepatitis*. JAMA. 1999; 282:1659-1664).

Figure 8:
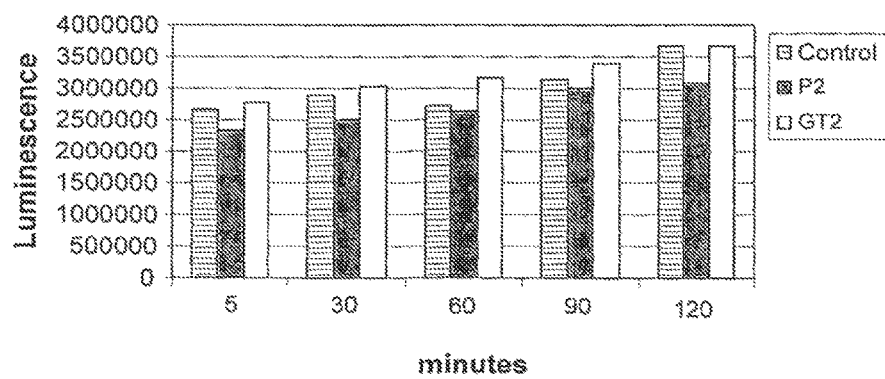
FIGS. 8 & 9 are bar graphs showing the production of ATP (as expressed in luminescence units) as a function of time in a liver cell line treated with 0.1 ml (FIG. 8) and 0.3 ml (FIG. 9) of *Hoodia* extracts.
Figure 9:
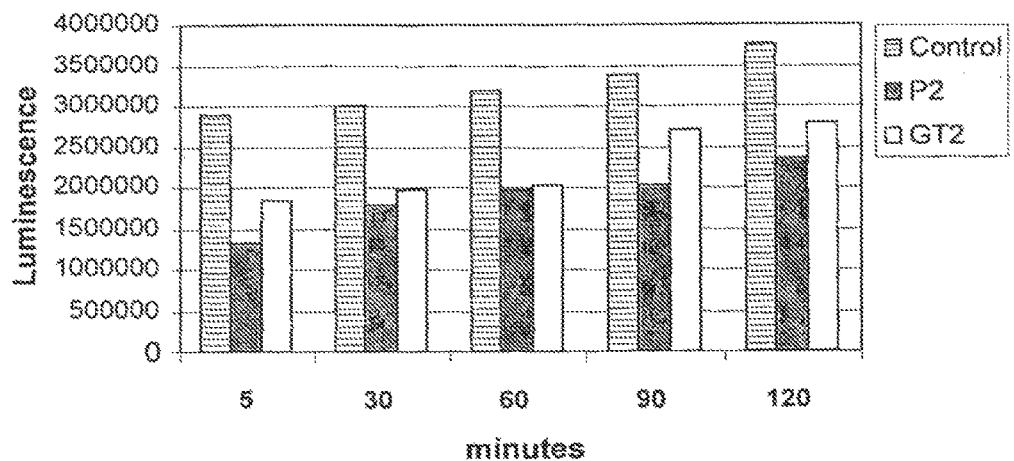

In order to investigate the effect of *Hoodia* extracts on liver metabolism, cells of a liver cell line (Hep3b) were incubated with different volumes of *Hoodia* extract, and ATP production was followed as a function of time by measuring luminescence production. The results are shown in FIGS. 8 (0.1 ml extract) and 9 (0.3 ml extract).

Example V

Phosphorylation of STAT3

STAT3 (signal transducer and activator of transcription 3) has been proposed to be the main mediator of acute phase (AP) gene induction downstream of IL-6 and other gp130 cytokines Phosphorylation of STAT3 leads to its activation and is considered important for immune modulation of liver function. Activation of STAT3 plays a role in acute phase response, protection against liver injury, promotion of liver regeneration, glucose homeostasis, and hepatic lipid metabolism. In this experiment, the effect of *Hoodia* extracts on the phosphorylation of STAT3 was determined.

Figure 10:
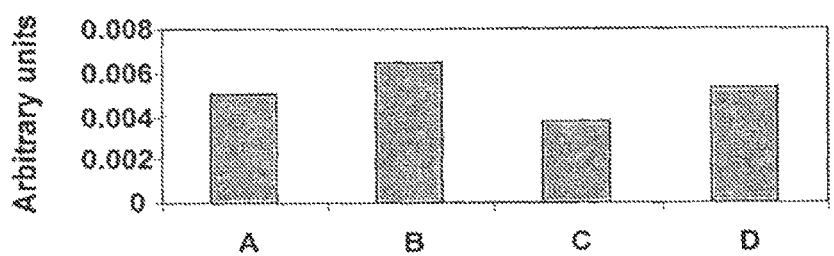
FIG. 10 is a bar graph showing the relative density of a Western Blot of phosphorylated STAT3 as compared to STAT3 for different groups of rats fed *Hoodia* extracts.

*Psammomys obesus* sand rats (4 rats per group) received daily po administrations of water, P2, SAP and GT2 (11 µl doses) for 4 weeks. The rats were sacrificed and the amount of phosphorylated STAT3 in the liver as compared to unphosphorylated STAT3, normalized with reference to β-actin, was measured by a Western Blot. The results (from 2 rats from each group) are shown in FIG. 10.

It may be seen that the rats which were fed *Hoodia Parviflora* showed a 29% increase in phosphorylated STAT3 as compared to the control. This shows that *Hoodia* extract can have a positive immunomodulatory effect on the liver.

Example VI

Safety and Efficacy of Oral Administration of *Hoodia* as a Medical Food for Patients with NAFLD The clinical trial was an open labeled dose escalation, safety study. The primary endpoints were based on the effect of treatment at one of the time points.

Subjects

The following protocol involved 10 men and women above 18 years with biopsy-proven NASH with a score of 4 or above, altered glucose metabolism, including diabetes (non treated, or treated with up to 2 drugs (not including insulin) without any change in medication 2 months prior to enrolment), impaired fasting glucose or impaired glucose tolerance.

Hoodia:

Method of preparation:
1. Harvesting the upper part of *Hoodia Parviflora* plant
2. Washing the fresh *Hoodia* plants with vibrating washing machine
3. Freezing the washed *Hoodia* plants (−200 C)
4. Cutting the frozen *Hoodia* plants to obtain cut *Hoodia* plant tissue—automatic cutting machine which cuts cubes of 1 cm2
5. Blending the solids particles are less than 100 micro meter—
6. First screening—400 micrometer filter, solids are being removed and the liquid is now the initial basic extract which is 100% pure blended plant tissue. From 1 Kg of plant tissue we get 800 ml of initial basic extract.
7. Adding 30% (v/v) water to the initial basic extract and blend the all mix under cold conditions (refrigerated tank 40 C)
8. Crushing the suspended *Hoodia* plant tissue (optionally further breaking and homogenizing the suspended *Hoodia* plant tissue in an ultrasonic bath)
9. Squeezing the solids via mechanical filter press (filter opening size is 300 micron)—the solids are being removed
10. Clarification of the squeezed liquid by using the SWECO vibration screener (200 and 100 micrometer)
11. Fast freezing the liquid in 3 ml containers, divided into individual doses and stored at a temperature of −20° C.
12. Each ml of final clear extract contained 0.8 gr of plant tissue. Oral administration was performed based on the dose currently used in medical foods containing *Hoodia* in western world countries.

*Hoodia* was prepared in liquid form as described below and was divided into 30 doses per patient and stored at a temperature of −20° C. All the drugs were stored at the study site.

Study Design:

*Hoodia* was administered in a dose of 0.043 ml/kg=34 mg/Kg. The patients were treated with this dose for 30 days.

During the treatment period, subjects ingested the *Hoodia* every day for 30 days, and were followed for clinical and laboratory effects (Table 1).

*Hoodia* was ingested in the morning before breakfast at the study site. The subjects were required to refrain from food for 2 hours after taking it.

HbA1C was between 5.5 and 14%. Blood was drawn for a complete blood count (CBC) and other laboratory analyses (see attached study plan in table 1). Serum was collected and archived for use in the development of surrogate markers. The subject visited the clinic on days 7, 14, 21, and 30. The Hoodia was taken every day for 30 days.

The subjects underwent a physical examination and blood samples were collected for all the disease parameters, as well as for T cell proliferation assay and FACS analysis for CD3, CD4, CD8, NKT, CD4CD25, FoxP3, CD4CCD25LAP.

TABLE 1

STUDY PLAN

| Day | Screen | 1 | 7 | 14 | 21 | 30 |
|---|---|---|---|---|---|---|
| Treatment (daily for days 1-30) |  | x | x | x | x | x |
| Informed Consent | X |  |  |  |  |  |
| Medical History | X |  |  |  |  |  |
| Medication History | X |  |  |  |  |  |
| AE Assessment | X | x | x | x | x | x |
| Physical Exam | X | X |  |  |  | X |
| Vital Signs | X | x | x | x | x | x |
| SMA[1] | X | X | X | X | X | X |
| CRP | X |  |  |  |  | X |
| CBC/differential | X | x | x | x | x | x |
| ESR | X |  |  |  |  | X |
| Pregnancy (βHCG) | X |  |  |  |  |  |
| FACS |  | X |  |  | x | X |
| In vitro cytokines |  | X |  |  | x | X |
| HOMA score | X |  |  |  | X | X |
| Glucose tolerance test | X |  |  |  |  | X |

[1]SMA includes: Total protein, albumin, ALT, AST, ALP, GGTP, LDH, total and LDL cholesterol, Triglycerides, uric acid, creatinine, urea (BUN), Na, K, glucose, total bilirubin Results The results regarding the effect on immune function are summarized in Table 2. It may be concluded from the results that oral administration of *Hoodia parviflora* was shown to be safe. In a large proportion of treated patients it induced a significant immunomodulatory effect and alleviated liver injury, improved insulin resistance and hyperlipidemia.

TABLE 2

|  | CD4 | CD25 | CD4 CD25 | CD4 + Foxp3 | CD4 + CD25 + Foxp3 | CD8 | CD8 + CD25 |
|---|---|---|---|---|---|---|---|
| Overall mean of response (%) | 10.3 | −121 | −100. | 8. | −7.8 | −15.6 | −5.3 |
| No. of responders | 6 | 6 | 7 | 6 | 6 | 10 | 6 |
| Mean for responders (%) | 17.2 | −224. | −160. | −12.3 | −33.3 | −15.6 | 51. |

|  | CD3 | CD56 | CD3 + CD56 | CD3 + CD69 | CD3 + CD69 + CD56 | CD62 | CD4 + CD62 |
|---|---|---|---|---|---|---|---|
| Overall mean of response (%) | −5.26 | −0.9 | 8.9 | −20.6 | 42.9 | −10.4 | −12.2 |
| No. of responders | 7 | 7 | 6 | 5 | 7 | 8 | 7 |
| Mean for responders (%) | −8.19 | 15.5 | 38.6 | −74. | 67.7 | −13.1 | −18.8 |

TABLE 2-continued

|  | CD4 + CD25 + HLA-DR | IVGTT AUC | IL-6 (pg/ml) | TNFα (pg/ml) | GLP-1 3 hours | GLP-1 0 |
|---|---|---|---|---|---|---|
| Overall mean of response (%) | −457. | 1645. | 8.9 | 5.9 | 27.6 | 27.2 |
| No. of responders | 9 | 7 | 5 | 5 | 4 | 1 |
| Mean for responders (%) | −508. | 8.9 | −37. | −92. | 2.08 | 1.67 |

|  | Ratio Adiponectin/IL-6 | Ratio Adiponectin/TNFα |
|---|---|---|
| Overall mean of response (%) | 1.3 | 1.3 |
| No. of responders | 8 | 7 |
| Mean for responders (%) | 17.5 | 25.9 |

The invention claimed is:

1. A method for treating a liver-related disease, the method comprising:
   administering to a mammal suffering from said liver-related disease an effective dosage of a water extract, sap, or powder preparation of a plant of genus *Hoodia*, wherein:
   said liver-related disease is an immune-mediated liver disease selected from the group consisting of fatty-infiltration, non-alcoholic fatty liver disease (NAFLD), cirrhosis of the liver, non-alcoholic steatohepatitis (NASH), and immune-mediated hepatitis; and
   said plant of genus *Hoodia* is any one of *Hoodia parviflora, Hoodia gordonii, Hoodia macrantha*, hybrid *Hoodia gordonii*, and mixtures thereof.

2. The method of claim 1, wherein the at least one *Hoodia* species is *Hoodia parviflora*.

3. The method of claim 1, wherein the extract is administered orally.

4. The method of claim 1, wherein the effective dosage is in the form of an edible composition selected from the group consisting of a dietary supplement, a nutraceutical, a food additive, a food product, and a beverage.

5. The method of claim 4, wherein the food product is an ice-cream or a frozen-cube.

6. A method for treating a liver-related disease, the method comprising:
   administering to a mammal suffering from said liver-related disease an effective dosage of a water extract, sap, or powder preparation of *Hoodia parviflora*,
   wherein said liver-related disease is an immune-mediated liver disease selected from the group consisting of non-alcoholic fatty liver disease (NAFLD), cirrhosis of the liver, non-alcoholic steatohepatitis (NASH), and immune-mediated hepatitis.

7. A method for treating a liver-related disease, the method comprising:
   administering to a mammal suffering from said liver-related disease an effective dosage of a water extract, sap, or powder preparation of *Hoodia parviflora*,
   wherein said liver-related disease is an immune-mediated liver disease selected from the group consisting of non-alcoholic fatty liver disease (NAFLD), non-alcoholic steatohepatitis (NASH), and immune-mediated hepatitis.

8. The method of claim 1, wherein said plant of genus *Hoodia* is any one of *Hoodia parviflora, Hoodia macrantha*, hybrid *Hoodia gordonii*, and mixtures thereof.

* * * * *